United States Patent [19]

Wright et al.

[11] Patent Number: 5,302,319
[45] Date of Patent: Apr. 12, 1994

[54] PREPARATION OF SOL GEL COMPOSITION FOR ELECTROPHORESIS

[75] Inventors: Robert J. Wright, Tequesta; William J. Dalzell, Jr., Jupiter, both of Fla.

[73] Assignee: United Technologies Corporation, Hartford, Conn.

[21] Appl. No.: 637,717

[22] Filed: Jan. 7, 1991

[51] Int. Cl.$^5$ .............................................. B01J 13/00
[52] U.S. Cl. .................................... 252/314; 252/309; 252/313.1; 106/287.17; 501/12
[58] Field of Search ...................... 252/309, 313.1, 314; 106/287.17; 501/12

[56] References Cited

U.S. PATENT DOCUMENTS

| | | | |
|---|---|---|---|
| 2,656,321 | 10/1953 | Hunter et al. | 252/313.1 |
| 3,445,361 | 5/1969 | Sicka et al. | 204/181.4 |
| 3,476,691 | 11/1969 | Smith et al. | 252/313.1 |
| 3,947,340 | 3/1976 | Kawagoshi et al. | 204/181 |
| 4,181,532 | 1/1980 | Woodhead | 252/313.1 X |
| 4,360,449 | 11/1982 | Oberlander et al. | 252/313.1 |
| 4,532,072 | 7/1985 | Segal | 252/313.1 |
| 4,801,399 | 1/1989 | Clark et al. | 252/315.01 |
| 4,921,731 | 5/1990 | Clark et al. | 427/314 |
| 5,047,174 | 9/1991 | Sherif | 252/309 |

OTHER PUBLICATIONS

Yoldas, "Alumina Sol Preparation from Alkoxides", American Ceramic Society Bulletin, vol. 54 No. 3 (1975), pp. 289-290.

Primary Examiner—Richard D. Lovering
Attorney, Agent, or Firm—Herbert W. Mylius

[57] ABSTRACT

A method is taught for the preparation of metal oxide sols particularly suited for the electrophoretic deposition of metal oxide coatings upon a fiber core.

14 Claims, No Drawings

PREPARATION OF SOL GEL COMPOSITION FOR ELECTROPHORESIS

TECHNICAL FIELD

The present invention relates to the general area of the application of ceramic materials to a substrate. More particularly, it relates to the preparation of sols of ceramic materials, such as the oxides of aluminum, yttrium, and mixtures thereof, such as Yttria-Alumina-Garnet, or YAG. The sols prepared by the process of the present invention are particularly suited for deposition on a fiber core by electrophoresis. When utilized for electrophoresis, the compositions prepared by the present invention provide even, dense, and uniform coatings, while avoiding the costly preparatory steps of prior art techniques for ceramic deposition on a substrate.

BACKGROUND ART

It is well known to apply coatings to the surface of a body so as to obtain surface properties which differ from those of the body. This may be done to achieve a variety of improvements, such as increased toughness, high temperature capability, wear resistance, and corrosion resistance. By providing surface coatings of the appropriate characteristics, it is possible to substantially lower the cost of an article built to specific property requirements. Ceramics have frequently been utilized to provide a surface coating over a less temperature resistant metallic article to permit use of that article in higher temperature environments. In addition, ceramic materials are frequently utilized to provide enhanced strength in metal matrix composites by inclusion in the form of powders, fibers, and whiskers. There is also a need for ceramic coated fibers for use in metal matrix composites, particularly those fibers coated with oxides, mixed oxides, or doped oxides, which coatings serve as diffusion or chemical barriers.

In the past, various processes have been used to deposit ceramic materials upon a substrate. These include the application of glazes, enamels, and coatings; hot-pressing materials at elevated pressure and temperature; and vapor deposition processes such as evaporation, cathodic sputtering, chemical vapor deposition, flame spraying, and plasma spraying. In addition, electrophoresis has been attempted, as have other specialized techniques, with limited success in application.

For example, the enamelling industry has used the electrodeposition of ceramic materials for some time. In the application of a ceramic coating by this technique, a ceramic material is milled or ground to a small particulate or powder size, placed into suspension, and electrophoretically deposited on the substrate. Another traditional method is the deposition of a ceramic coating from a slurry made up of a powder in suspension, usually in an aqueous medium. A major problem with these techniques is that powder particle sizes below about 2 microns were difficult to obtain, thus limiting the quality of coatings produced.

Sol-gel technology has recently evolved as a source of very fine sub-micron ceramic particles of great uniformity. Such sol-gel technology comprises essentially the preparation of ceramics by low temperature hydrolysis and peptization of metal oxide precursors in solution, rather than by the sintering of compressed powders at high temperatures.

In the prior art, much attention has been given to the preparation of sols of metal oxides (actually metal hydroxide) by hydrolysis and peptization of the corresponding metal alkoxide, such as aluminum sec-butoxide [$Al(OC_4H_9)_3$], in water, with an acid peptizer such as hydrochloric acid, acetic acid, nitric acid, and the like. The hydrolysis of aluminum alkoxides is discussed in an article entitled "Alumina Sol Preparation from Alkoxides" by Yoldas, in American Ceramic Society Bulletin Vol. 54, No. 3 (1975), pages 289-290. This article teaches the hydrolysis of aluminum alkoxide precursor with a mole ratio of water:precursor of 100:1, followed by peptization at 90° with 0.07 moles of acid per mole of precursor. After gelling and drying, the dried gel is calcined to form alumina powder.

In U.S. Pat. No. 4,532,072, of Segal, an alumina sol is prepared by mixing cold water and aluminum alkoxide in stoichiometric ratio, allowing them to react to form a peptizable aluminum hydrate, and peptizing the hydrate with a peptizing agent in an aqueous medium to produce a sol of an aluminum compound.

In Clark et al, U.S. Pat. No. 4,801,399, a method for obtaining a metal oxide sol is taught whereby a metal alkoxide is hydrolysed in the presence of an excess of aqueous medium, and peptized in the presence of a metal salt, such as a nitrate, so as to obtain a particle size in the sol between 0.0001 micron and 10 microns.

In Clark et al, U.S. Pat. No. 4,921,731, a method is taught for ceramic coating a substrate by thermophoresis of sols of the type prepared by the method of U.S. Pat. No. 4,801,399. In addition, Clark et al, in abandoned U.S. patent application 06/841,089, filed Feb. 25, 1986, teach formation of ceramic coatings on a substrate, including filaments, ribbons, and wires, by electrophoresis of such sols. However, the examples of this application indicate that the coatings obtained using electrophoresis were uneven, cracked, and contained bubbles, and often peeled, flaked off, and/or pulled apart. Throughout, the evolution of hydrogen bubbles at the cathode during electrophoresis was noted.

It is thus seen that a need exists for a sol which is suitable for the electrophoretic deposition of uniform ceramic coatings on a substrate such as a filament, fiber tow, or wire.

SUMMARY OF THE INVENTION

In the pursuit of a method for the preparation of defect-free ceramic coatings, applicants have developed a novel metal oxide sol which is particularly suited for use in an electrophoretic deposition process. This sol is especially suitable for the preparation of ceramic coated fibers, and ceramic fibers. As used herein, the term "filament" shall refer to a single strand of fibrous material, "fiber tow" shall refer to a multi-filament yarn or array or filaments, a "wire" shall refer in general to metallic filaments or tows, a "fiber core" shall refer to a filament, fiber tow, or wire suitable for coating by the sol produced by the process of this invention, and the term "ceramic coated fiber" or "coated fiber" shall refer to a fiber core of an electrically conductive material, or a material which has been made to be conductive such as by a flash coat of carbon or a metallizing layer, upon which has been deposited a uniform ceramic layer, such that the diameter of the fiber core is greater than the thickness of the applied ceramic. Conversely, for convenience, the term "ceramic fiber" or "fiber" shall refer to an electrically conductive fiber core material upon which has been deposited a uniform ceramic layer, such that the thickness of the ceramic layer exceeds the diameter of the fiber core. In either case, of course, the fiber core material may be removed by such techniques as acid dissolution, combustion, etc., to leave a hollow ceramic cylinder, which may, of course, then be referred to as a ceramic fiber.

It is an object of the present invention to provide a method for making a sol suitable for electrophoretic deposition on a filament, fiber tow, or wire. It is a further object of this invention to provide a method for the preparation of a sol which may be deposited on a fiber core by electrophoresis so as to provide a ceramic coated fiber or ceramic fiber. It is a still further object of this invention to produce a sol which may be utilized to obtain a highly uniform, defect-free ceramic coating, or a ceramic fiber up to 10 mils in diameter.

The present invention provides a method for the preparation of a sol suitable for use in electrophoresis, said method comprising the steps of:

a) hydrolysing a precursor organometallic compound in an aqueous medium comprising water and an organic solvent, the molar ratio of precursor organometallic compound to water being from about 0.005 to about 0.03, the molar ratio of organic solvent to precursor organometallic compound being from about 1.0 to about 5.0;

b) adding to the reaction mixture a peptizing agent, in a molar ratio of from about 0.05 to about 0.3 moles of peptizer per mole of precursor organometallic compound, and permitting the sol to clear;

c) permitting the sol to cool and removing at least 90 percent of the separated organic solvent phase;

d) reducing the volume of the remaining sol to from about 50 percent to about 75 percent of its previous volume by evaporation; and e) re-alcoholizing said sol by adding thereto sufficient alcohol to provide a molar ratio of added alcohol to metallic hydrate of from about 50 to about 70.

The present invention further comprises a method for the preparation of a metal oxide sol having properties suitable for electrophoresis, said method comprising the steps of:

a) reacting a mixture comprising a metal alkoxide, water and organic alcohol, the molar ratio of said alkoxide to said water being from about 0.006 to about 0.02, and the molar ratio of said organic alcohol to said alkoxide being from about 1.8 to about 3.2;

b) peptizing the reaction mixture, the peptizer being selected from the group consisting of hydrochloric acid, nitric acid, acetic acid, formic acid, and aluminum nitrate, the molar ratio of peptizer to said alkoxide being from about 0.08 to about 0.23, thereby forming a clear sol;

c) removing at least 95 percent of the excess organic alcohol and water from said sol;

d) heating the remaining sol to reduce the volume thereof to from about 58 percent to 72 percent of its previous volume; and e) recovering said sol.

The present invention also comprises a method for the preparation of a sol for the electrophoretic deposition of a ceramic coating on a fiber core, said method comprising;

a) reacting a reaction mixture comprising aluminum sec-butoxide, water, and 2-butanol, the molar ratio of said butoxide to said water being from about 0.008 to about 0.15, and the molar ratio of said butanol to said butoxide being from about 2.3 to about 2.7;

b) peptizing said reaction mixture with an acid peptizer so as to provide a molar ratio of said acid to butoxide of from about 0.125 to about 0.175;

c) removing from said peptized reaction mixture at least about 98 percent of the excess butanol and water;

d) reducing the remaining reaction mixture to from about 60 percent to about 70 percent of its previous volume; and e) mixing the thus concentrated reaction mixture with alcohol to provide an electrophoretic sol in which the molar ratio of alcohol to metal hydrate is from about 58 to about 67.

DETAILED DESCRIPTION OF THE INVENTION

The present invention comprises a method for the preparation of a sol specifically formulated for the purpose of providing a medium for the electrophoretic deposition of metal oxide coatings on a fiber core, and the sol per se.

The sol of the present invention is suitable for use in producing either ceramic coated fibers, or ceramic fibers. In addition, the sol disclosed herein ma be used to produce multi-layer coatings of ceramic, or to obtain composite materials by the incorporation of filler materials therein prior to electrophoresis.

The sols of the present invention may be produced from a variety of organometallic compounds, to yield metal oxides such as alumina, chrome-ion doped alumina, yttria, and mixtures thereof, such as Yttria-Alumina-Garnet (YAG), $3Y_2O_3.5Al_2O_3$. Further, while the present disclosure is specific to chrome-ion doped oxides, other metal doping ions may also be utilized.

Electrophoresis is an electrodeposition technique whereby minute particles of a normally nonconductive material in colloidal suspension are subjected to an external electric field and thus caused to migrate toward a specific electrode. Colloids in solution are known to develop a surface charge relative to the suspension medium, as a result of any of a number of possible mechanisms, such as lattice imperfection, ionization, ion absorption, and ion dissolution. In the case of metal oxides such as alumina, the surface charge is the result of ionization, and is generally positive in the preferred pH range, below about 7.

During electrophoresis, the positively charged colloids migrate toward the cathode, forming a compact layer of particles thereupon. The physical properties of the deposited coatings are related to their compaction on, and adherence to, the substrate. Generally, the greater the compaction of the colloidal particles deposited upon the substrate, the better the mechanical properties of the coating and the greater the protection afforded thereby.

The sols of the present invention may be utilized to electrophoretically deposit coatings on a wide range of substrates, both metallic and non-metallic, which substrates are electrically conductive or made to be conductive for use. Exemplary substrate materials include carbon, glass, silicon carbide, silicon nitride, and metals such as aluminum, iron, nickel, tantalum, titanium, molybdenum, tungsten, rhenium, niobium, and alloys thereof. In general, any material known to be electrically conductive, or which can be made electrically conductive, may be utilized. The sols of this invention are particularly applicable to filaments, fiber tows, and wires of such materials.

In accordance with the present invention, organometallic compounds are hydrolyzed and peptized to obtain a sol having a colloidal particle size of from about 10 Angstroms to about 150 Angstroms. A preferred range of particle size is from about 50 Angstroms to about 100 Angstroms. Within these ranges of particle sizes, good contact of the coating materials is attained with the substrate, giving excellent adhesion, and excellent packing of the coating particles within the coating layer is obtained, resulting in superior coating properties such as wear resistance, and thermal high temperature capability.

The process of the present invention comprises a method for preparation of sols for the express purpose of electrophoresis. To achieve this goal, it is necessary to achieve a colloid sol having very small particle size, e.g. less than about 150 Angstroms in diameter. We have found that this may be achieved by the use of a process which differs from the prior art in that hydrolysis of the metallic precursor occurs in the presence of a molar excess of organic solvent, a dehydration/de-alcoholization step occurs after peptization, and after concentration of the sol by removal of water by such means as evaporation, an alcohol transfer reintroduces alcohol in a molar ratio of up to 70 moles of alcohol per mole of metal hydrate present. While the phase transformation reactions occurring during the specific order of the steps of this process are not fully understood, it is theorized that cross-linkage of the AlOOH species during the dewatering and de-alcoholization steps results in a final coating after electrophoretic deposition which is less prone to cracking, spallation, peeling, or flaking. The re-addition of alcohol after concentration of the sol, i.e. re-alcoholization, results in the production of extremely small colloid particles, and an extremely stable sol having a long shelf life and favorable characteristics for electrophoresis. It is to be noted that individual processes may be tailored for differing materials, by choice of organic solvent, peptizer, and additive alcohol utilized.

In general, the process is comprised of the following steps:

a) concurrent hydrolysis and alcoholization of an organometallic compound in an aqueous medium comprising water and an organic solvent;

b) peptization of this reaction mixture with a monovalent acid or acid source;

c) dehydration and de-alcoholization of the reaction mixture by removal of the excess aqueous phase, e.g. by decanting or pipetting;

d) dewatering and further removal of unreacted alcohol by evaporation, also referred to as concentration and/or volume reduction, generally by a vigorous boiling; and e) re-alcoholization or introduction of additional alcohol to the concentrated sol to form a sol suitable for electrophoresis.

The above procedure is subject to very close control of the proportions of materials utilized, and their molar ratios at the various stages of the procedure. Table I sets forth broad, preferred, and most preferred ranges of the molar ratios of materials during the steps of this procedure, as well as the extent of dewatering/de-alcoholization and volume reduction of the sol.

TABLE I

| Parameter | Broad | Preferred | Most Preferred |
|---|---|---|---|
| Molar ratio, organometallic compound to water | 0.005–0.03 | 0.006–0.02 | 0.008–0.15 |
| Molar ratio, organic solvent to organometallic compound | 1.0–5.0 | 1.8–3.2 | 2.3–2.7 |
| Molar ratio, peptizer to organometallic compound | 0.05–0.3 | 0.08–0.23 | 0.125–0.175 |
| Percentage of excess aqueous phase removed during dehydration/de-alcoholization | 90–100 | 95–100 | 98–100 |
| Percentage of volume reduction during dewatering (concentration) | 50–75 | 58–72 | 60–70 |
| Molar ratio, added alcohol to metal hydrate in the concentrated sol | 50–70 | 55–69 | 58–67 |

In general, the sols of the present invention may be prepared by the hydrolysis and peptization of the corresponding organometallic compounds in an aqueous medium. Preferred organometallic compounds are metal alkoxides, and particularly the metal sec-butoxides, ethoxides, and methoxides. The metal alkoxides may be alkoxides of aluminum, and yttrium, and mixtures thereof.

The aqueous medium utilized in the preparation of the sols of the present invention comprises a solution of water, preferably deionized or distilled, and an organic solvent, such as an organic alcohol, aldehyde, or ketone. Suitable organic solvents include ethyl alcohol, methyl alcohol, isopropanol, butanol, and acetone.

The peptizer utilized in the present invention may be selected from monovalent acids, such as hydrochloric, nitric, acetic, and formic acids, or inorganic acid forming salts such as aluminum nitrate. It is envisioned that the process of the present invention may also be successful using a basic peptizer rather than an acidic peptizer. In such case, the subsequent use of the sol in an electrophoretic deposition process would be subject to a reversal of polarity of the electrodes employed.

The hydrolysis, alcoholization, and peptizing procedure may be conducted at temperatures of from about 80° to about 98° C., preferably from about 88° to about 93° C., and most preferably at about 90° C. The length of time for the reactions may be varied in accordance with the reaction temperatures and proportions of the components present in the hydrolysis/alcoholization/peptization mixture. Preferred times for the reaction and peptization are from a matter of seconds to weeks, but preferably between one minute and one week, and more preferably between 10 minutes and 24 hours.

The alcohol added to the concentrated sol may be selected from methanol, ethanol, isopropanol, butanol, etc. Some surface charge effect variation is noted with variance of the alcohol used. In the preparation of aluminum hydrate sols, methanol and ethanol are the preferred alcohols, while in the preparation of YAG sols, ethanol is preferred.

The sol of the present invention may be prepared in the following manner, with particular attention being given to prevention of exposure of the reaction mixture to air. While the examples are specific to the preparation of alumina forming sol-gels formulated from an aluminum sec-butoxide precursor, the invention is not to be limited thereto.

Example 1

For the preparation of an alumina sol, a 4000 ml glass reaction vessel was assembled with a variable temperature heating mantel, a glass TEFLON polytetrafluoroethylene resin stirring rod with a laboratory mixer having variable speed control, an injection port with a TEFLON tube for insertion of liquids to the bottom of the reaction vessel, and a water-cooled PYREX condenser. After turning on the flow of cooling water to the condenser, 2500 grams (corresponding to 138.8 moles or 2500 ml) of deionized water was metered into the closed reaction vessel, after which the heating mantel was turned on to raise the temperature of the water to between 88° C. and 93° C., which temperature was thereafter maintained. The mixer motor was turned on when the water had reached this temperature, and the water was vigorously stirred. In a separately sealable glass transfer container 357.5 grams (corresponding to 1.5 moles or 357.5 ml) of aluminum sec-butoxide [Al(OC$_4$H$_9$)$_3$] was mixed with 288.86 grams (corresponding to 3.897 moles or 357.5 ml) of 2-butanol. Experience has taught that exposure of this mixture, or the aluminum sec-butoxide, to air for any longer than the absolute minimum necessary adversely affected the sol produced, so great care was exercised to avoid exposure. The mixture of sec-butoxide and butanol, in the transfer container, was connected to the reaction vessel entry port after the water had reached the desired temperature, and very slowly, over a 5 minute period, metered directly down into the hot deionized water. When all of the mixture had been introduced into the water, the entry port was valved shut and the transfer container removed. The mixture of water, sec-butoxide, and butanol was then permitted to hydrolyse and reflux for a period of 1 hour at temperature while stirring vigorously.

After 1 hour, and with the mixture still at temperature and being refluxed and stirred vigorously, the sol mixture was peptized by connecting a glass syringe containing 8.18 grams (0.224 moles or 6.875 ml) of hydrochloric acid to the vessel entry port. The entry valve was opened and the acid metered directly down into the sol mixture. The valve was then closed, and the syringe removed and refilled with air. The syringe was then reconnected to the entry port, and the air injected into the vessel to ensure that all of the acid had been introduced into the system. The valve was then closed, and the syringe removed.

The heating, stirring, and refluxing were maintained until the sol cleared, about 16 hours. The heat was then turned off and the stirrer and motor assembly removed. After the mixture cooled, the sol and alcohol separated, and the alcohol was removed by pipette. It was found that leaving a small amount of alcohol in the sol did not adversely affect the sol. The pH of the sol was measured and found to be pH 3.90. This initial sol was found to have a good shelf life, and could be stored prior to further processing to obtain a suitable electrophoresis bath.

A sol was specifically formulated for the express purpose of making fibers and/or coating fibers in a continuous process. This specific formulation was also found to be suitable for coating fibers or other substrates with a composite coating material, wherein the composite included any chopped fiber material, platelets, powder, or particulates, of metals or other materials in the alumina matrix.

This sol was derived from the initial sol prepared above. A 390 ml sample of the sol prepared above was heated in an open glass beaker to a temperature of approximately 93° C., and the volatiles, alcohol and excess water, evaporated off. The sol was heated until it had been reduced to 250 ml, i.e. to 64 percent of its initial volume, with a noted increase in viscosity. The reduced sol was then removed from the heat and permitted to cool to room temperature. The reduced sol was then re-alcoholized with 750 ml of ethyl alcohol (63 moles of alcohol/mole of aluminum hydrate present). The sol and alcohol were vigorously mixed, then sealed in an air tight container for storage. The pH of this sol was about pH 3.8. This sol was set aside for 5 months, demonstrating good shelf life, and then subjected to electrophoretic deposition. The sol was found to successfully yield dense coatings by electrophoresis. Further, when a filler was added to the electrophoretic bath, a composite fiber of alumina and dispersed filler material was obtained.

The sols prepared in accordance with the present invention demonstrate utility for electrophoretic deposition, and in particular for the electrophoretic deposition of ceramic forming coatings on fiber cores, or ceramic fibers per se. Such coatings and fibers have great potential for use as reinforcement fibers in various matrix composites.

It is to be understood that the above disclosure of the present invention is subject to considerable modification, change, and adaptation by those skilled in the art, and that such modifications, changes, and adaptations are to be considered to be within the scope of the present invention, which is set forth by the appended claims.

We claim:

1. A method for the preparation of a sol suitable for use in electrophoresis, said method comprising the steps of:
   a) hydrolysing a precursor organometallic compound by heating at a temperature of from about 80° to about 90° C. in an aqueous medium comprising water and an organic solvent, the molar ratio of precursor organometallic compound to water being from about 0.005 to about 0.03, the molar ratio of organic solvent to precursor organometallic compound being from about 1.0 to about 5.0;
   b) adding to the reaction mixture a peptizing agent, in a molar ratio of from about 0.05 to about 0.3 moles of peptizer per mole of precursor organometallic compound, and permitting the sol to clear;
   c) permitting the sol to cool and removing at least 90 percent of the separated aqueous phase;
   d) reducing the volume of the remaining sol to from about 50 percent to about 75 percent of its previous volume by evaporation; and
   e) adding thereto sufficient alcohol to provide a molar ratio of added alcohol to metallic hydrate of from about 50 to about 70.

2. A method as set forth in claim 1, wherein said organometallic compound is a metal alkoxide.

3. A method as set forth in claim 2, wherein said metal alkoxide is selected from the group consisting of the sec-butoxides, ethoxides, and methoxides of aluminum and yttrium, metal ion-doped aluminum and yttrium, and mixtures thereof.

4. A method as set forth in claim 3, wherein said sol is selected from the group consisting of alumina, chrome-ion doped alumina, and yttria.

5. A method as set forth in claim 3, wherein said organic solvent is selected from the group consisting of organic alcohols, aldehydes, and ketones.

6. A method as set forth in claim 5, wherein said organic solvent is selected from the group consisting of ethyl alcohol, methyl alcohol, isopropanol, butanol, and acetone.

7. A method as set forth in claim 6, wherein the molar ratio of organic solvent to metal alkoxide is from about 1.8 to about 3.2.

8. A method as set forth in claim 7, wherein the molar ratio of organic solvent to metal alkoxide is from about 2.3 to about 2.7.

9. A method as set forth in claim 5, wherein said peptizing agent is selected from the group consisting of hydrochloric, nitric, acetic, and formic acids, and aluminum nitrate.

10. A method as set forth in claim 9, wherein the molar ratio of said peptizing agent to said metal alkoxide is from about 0.08 to about 0.23.

11. A method as set forth in claim 9 wherein said added alcohol is selected from the group consisting of methanol and ethanol.

12. A method for the preparation of a metal oxide sol comprising the steps of:
 a) reacting a mixture comprising a metal alkoxide, water and organic alcohol, the molar ratio of said alkoxide to said water being from about 0.006 to about 0.02, and the molar ratio of said organic alcohol to said alkoxide being from about 1.8 to about 3.2;
 b) peptizing the reaction mixture, the peptizer being selected from the group consisting of hydrochloric acid, nitric acid, acetic acid, formic acid, and aluminum nitrate, the molar ratio of peptizer to said alkoxide being from about 0.08 to about 0.23, thereby forming a clear sol;
 c) removing at least 95 percent of the excess organic alcohol and water from said sol;
 d) heating the remaining sol to reduce the volume thereof to form from about 58 percent to 72 percent of its previous volume;
 e) recovering said sol, and mixing said recovered sol with additional alcohol such that the molar ratio of said alcohol to the metal hydrate is from about 55 to about 69.

13. A method for the preparation of a sol for the electrophoretic deposition of a ceramic coating on a fiber core, said method comprising the steps of:
 a) reacting a reaction mixture comprising aluminum sec-butoxide, water, and 2-butanol, the molar ratio of said butoxide to said water being from about 0.008 to about 0.15, and the molar ratio of said butanol to said butoxide being from about 2.3 to about 2.7;
 b) peptizing said reaction mixture with an acid peptizer so as to provide a molar ratio of said acid to butoxide of from about 0.125 to about 0.175;
 c) removing from said peptized reaction mixture at least about 98 percent of the excess butanol and water;
 d) reducing the remaining reaction mixture to from about 60 percent to about 70 percent of its previous volume; and
 e) mixing the thus concentrated reaction mixture with alcohol to provide an electrophoretic sol in which the molar ratio of alcohol to metal hydrate is from about 58 to about 67.

14. A method as set forth in claim 13, wherein said molar ratio of butoxide to water is about 0.011, said molar ratio of butanol to butoxide is about 2.6, said molar ratio of peptizer to butoxide is about 0.15, the reaction mixture is concentrated to about 64 percent of its volume, and said added alcohol is ethyl alcohol in a molar ratio of about 63 moles per mole of aluminum hydrate present.

* * * * *